(12) United States Patent
Nozaki et al.

(10) Patent No.: US 12,742,143 B2
(45) Date of Patent: Sep. 22, 2026

(54) CELL SHEET CUTTING ASSISTANCE SYSTEM, CELL CULTURE SYSTEM AND CELL SHEET CUTTING ASSISTANCE METHOD

(71) Applicant: Hitachi, Ltd., Tokyo (JP)

(72) Inventors: Takayuki Nozaki, Tokyo (JP); Yuki Niimi, Tokyo (JP); Masaharu Kiyama, Tokyo (JP); Kakuro Hirai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 749 days.

(21) Appl. No.: 18/108,527

(22) Filed: Feb. 10, 2023

(65) Prior Publication Data

US 2023/0407228 A1 Dec. 21, 2023

(30) Foreign Application Priority Data

Jun. 15, 2022 (JP) ................................ 2022-096504

(51) Int. Cl.

| | |
|---|---|
| ***C12M 1/36*** | (2006.01) |
| ***C12M 1/32*** | (2006.01) |
| ***C12M 1/34*** | (2006.01) |
| ***C12Q 1/02*** | (2006.01) |

(52) U.S. Cl.

CPC ............ *C12M 41/48* (2013.01); *C12M 23/12* (2013.01); *C12M 41/46* (2013.01); *C12Q 1/02* (2013.01)

(58) Field of Classification Search

CPC .... C12M 41/48; C12M 41/46; C12M 45/052; C12M 23/12; C12M 21/08; C12Q 1/02

See application file for complete search history.

(56) References Cited

U.S. PATENT DOCUMENTS

| | | | | |
|---|---|---|---|---|
| 5,998,129 | A * | 12/1999 | Schutze ................ | B01L 3/0244 435/40.52 |
| 2008/0166329 | A1* | 7/2008 | Sung ...................... | A61K 35/34 604/506 |
| 2012/0052524 | A1* | 3/2012 | Kinooka ................ | C12Q 1/025 435/287.1 |
| 2017/0166948 | A1 | 6/2017 | Matsumoto | |
| 2020/0362310 | A1 | 11/2020 | Sameshima et al. | |

FOREIGN PATENT DOCUMENTS

| | | | |
|---|---|---|---|
| JP | 2000-504824 | A | 4/2000 |
| JP | 2016-054724 | A | 4/2016 |
| TW | 201940694 | A | 10/2019 |
| WO | 2010/137739 | A1 | 12/2010 |
| WO | 2015/107667 | A1 | 7/2015 |

* cited by examiner

*Primary Examiner* — Michael L Hobbs

(74) *Attorney, Agent, or Firm* — PROCOPIO, CORY, HARGREAVES & SAVITCH LLP

(57) ABSTRACT

A cell sheet cutting assistance system comprises a processor for executing a program and a storage device for storing the program. The processor: receives, as input, an evaluation standard of a cell sheet and quality information of a cultured cell sheet; determines whether the quality information satisfies the evaluation standard; and outputs a cutting position of the cell sheet based on a result of the determination.

17 Claims, 12 Drawing Sheets

100
102
MEDICAL INSTITUTION / PHARMACEUTICAL COMPANY
EVALUATION STANDARD
CELL SHEET
CELL SHEET CUTTING ASSISTANCE SYSTEM
QUALITY INFORMATION / EVALUATION STANDARD
CUTTING POSITION
QUALITY INFORMATION INQUIRY
QUALITY INFORMATION REPLY
101
MEDICAL INSTITUTION / PHARMACEUTICAL COMPANY / CELL SHEET PRODUCING COMPANY

FIG 3A

PATIENT DATBASE

| | EVALUATION STANDARD | | | | CULTURE CONDITION | |
|---|---|---|---|---|---|---|
| No. | CELL TYPE | NUMBER OF CELLS | THICKNESS OF CELL SHEET | NUMBER OF SHEETS | CULTURE PERIOD | CULTURE MEDIUM REPLACEMENT FREQUENCY |
| 1 | ○○CELL | ●● × $10^6$ cells | ○μm | 3 sheets | 14 days | 1 per day |
| 2 | △△CELL | ●● × $10^6$ cells | ○μm | 8 sheets | 21 days | 1 per day |
| 3 | ○△CELL | ●● × $10^6$ cells | ○μm | 5 sheets | 28 days | 1 per day |

FIG 3B

CELL CULTURE DATABASE

| No. | POSISION INFORMATION OF CULTURE CONTAINER | OBSERVATION RESULT | | MONITORING RESULT | |
|---|---|---|---|---|---|
| | | 9TH DAY OF CULTURE | 10TH DAY OF CULTURE | 9TH DAY OF CULTURE | 10TH DAY OF CULTURE |
| 1 | $(x_1, y_1)$ | NUMBER OF CELLS. :<br>●● × $10^6$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | NUMBER OF CELLS:<br>●● × $10^7$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | pH:○<br>Glc: | pH:○<br>Glc:△ |
| 2 | $(x_2, y_2)$ | NUMBER OF CELSS:<br>●● × $10^6$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | NUMBER OF CELLS:<br>●● × $10^7$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | pH:○<br>Glc:△ | pH:○<br>Glc:△ |

FIG 3C

IDENTIFICATION INFORMATION DATABASE

| No. | IDENTIFICATION INFORMATION | POSITION INFORMATION OF CULTURE CONTAINER | OBSERVATION RESULT | | MONITORING RESULT | |
|---|---|---|---|---|---|---|
| | | | 13TH DAY OF CULTURE | 14TH DAY OF CULTURE | 13TH DAY OF CULTURE | 14TH DAY OF CULTURE |
| 1 | AB100 | $(x_1, y_1)$ | NUMBER OF CELLS: ●● × $10^6$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | NUMBER OF CELLS: ●● × $10^7$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | pH:○<br>Glc:△ | pH:○<br>Glc:△ |
| 2 | AB200 | $(x_2, y_2)$ | NUMBER OF CELLS: ●● × $10^6$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | NUMBER OF CELLS: ●● × $10^7$ cells<br>CELL OCCUPANCY: ○○%<br>SHEET THICKNESS: △△μm<br>WHETHER THERE IS A HOLE: ...<br>CELL DENSITY: ...<br>CELL SURVIVAL RATE: ... | pH:○<br>Glc:△ | pH:○<br>Glc:△ |

FIG 3D

PATIENT DATABASE

| | PATIENT INFORMATION | | | | | EVALUATION STANDARD | | | CULTURE CONDITION | |
|---|---|---|---|---|---|---|---|---|---|---|
| No. | PATIENT ID | GRAFTING MEDICAL INSTUTITION | SIZE OF AFFECTED PART | SIZE AND SHAPE OF CELL SHEET | NUMBER OF SHEES | CELL TYPE | SIZE OF CELL SHEET | THICKNESS OF CELL SHEET | CULTURE PERIOD | CULTURE MEDIUM REPLACEMENT FREQUENCY |
| 1 | SDCX23098 | ○□ hospital | ○○ $cm^2$ | diameter 3cm circle | 3 sheets | ○○ cell | ○○$cm^2$ | ○$cm^2$ | 14 days | 1 per day |
| 2 | IKED39875 | △◇ hospital | △△ $cm^2$ | height 5cm, width 2cm rectangle | 8 sheets | △△ cell | ○○$cm^2$ | ○$cm^2$ | 21 days | 1 per day |
| 3 | QOIY04957 | □○ hospital | □□ $cm^2$ | height 2cm, base 3cm triangle | 5 sheets | ○△ cell | ○○$cm^2$ | ○$cm^2$ | 28 days | 1 per day |

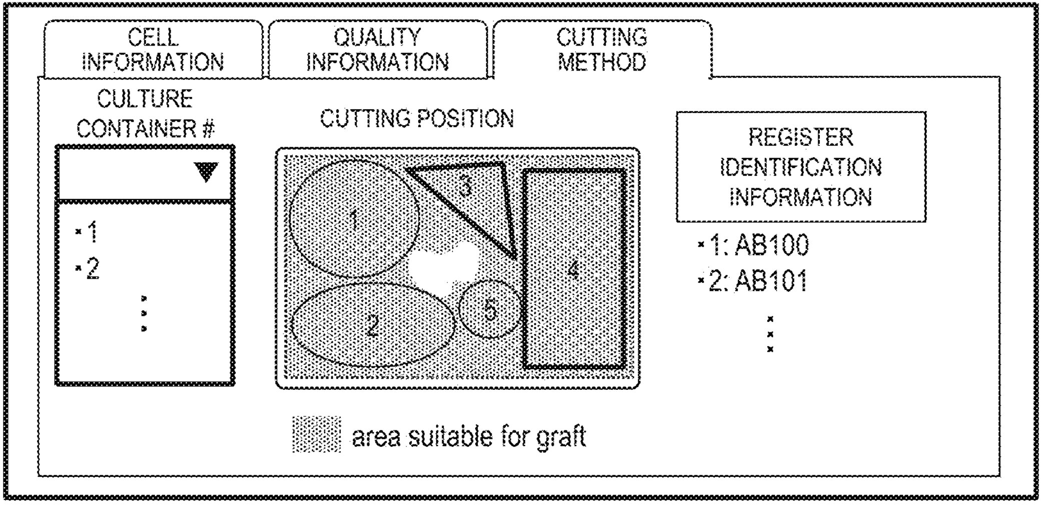

FIG 8

| | PROGNOSIS INFORMATION | | | | | QUALITY INFORMATION | | CULTURE CONDITION | |
|---|---|---|---|---|---|---|---|---|---|
| No. | PATIENT ID | GRAFTED CELL TYPE | SIZE OF AFFECTED PART | SIZE OF GRAFTED CELL SHEET | TREAT-MENT EFFECT | SIZE OF CELL SHEET | THICKNESS OF CELL SHEET | CULTURE PERIOD | CULTURE MEDIUM REPLACEMENT FREQUENCY |
| 1 | SDCX23098 | ○○ cell | ○○cm2 | ○○cm2 | 80 | ○○cm2 | ○μm | 14 days | 1 per day |
| 2 | IKED39875 | △△ cell | △△cm2 | △△cm2 | 70 | △△cm2 | ○μm | 21 days | 1 per day |
| 3 | QOIY04957 | ○△ cell | □□cm2 | □□cm2 | 90 | □□cm2 | ○μm | 28 days | 1 per day |
| 4 | HHJL88763 | ◇◇ cell | ◇◇cm2 | ◇◇cm2 | 30 | ◇◇cm2 | ○μm | 7 days | 1 per day |
| 5 | PIMJ09733 | ○△ cell | ○△cm2 | ○△cm2 | 50 | ○△cm2 | ○μm | 3 days | 1 per day |
| 6 | QOCS87305 | □◇ cell | □◇cm2 | □◇cm2 | 80 | □◇cm2 | ○μm | 14 days | 1 per day |

CELL SHEET CUTTING ASSISTANCE SYSTEM, CELL CULTURE SYSTEM AND CELL SHEET CUTTING ASSISTANCE METHOD

CROSS REFERENCE TO RELATED APPLICATIONS

The present application claims priority from Japanese patent application JP 2022-096504 filed on Jun. 15, 2022, the entire content of which is hereby incorporated by reference into this application.

BACKGROUND

Technical Field

The present invention relates to a cell sheet cutting assistance system, a cell culture system and a cell sheet cutting assistance method.

Background Art

Regenerative medicine for recovering function of organs or the like is expected to be radical cure for diseases with no treatment traditionally. One of representative graft forms in regenerative medicine is cell sheet wherein cells are joined together or cells and extracellular matrices are joined. Regarding the cell sheet, studies are in progress for treatments for wide variety of sites such as skin, cornea, heart, cartilage, esophagus, etc., and some have been commercialized. Also, based on demand for cell sheets expected in the future, development is required for a technique for culture and produce a plurality of cell sheets in bulk at a time in order to supply the cell sheets with certain quality industrially stably. Recently, reduction of production cost is expected to be possible by producing cell sheets in bulk at a time for allogamy so that cell sheets for a plurality of patients can be prepared at a time.

On the other hand, a cell sheet is a three-dimensional organization from raw material of cells, and it is difficult to culture it completely uniform with respect to density of cells constituting the cell sheet, thickness of the cell sheet, etc. Also, quality of cell sheet may differ depending on conditions of cells to be the raw material, the culture container or the position within the culture container. Further, it becomes more difficult to maintain certain quality of the cell sheet with larger culture containers.

JP 2016-054724 A discloses a cell culture evaluation system which performs culture while changing placement of plurality of wells which are units for cell culture and evaluate quality for each well.

SUMMARY

JP 2016-054724 A does not consider cutting one cell sheet. Accordingly, a step for finding a portion to be cut from a region of a cell sheet satisfying a predetermined quality condition is troublesome.

Accordingly, the present invention facilitates the step for finding the portion to be cut in the cell sheet.

An example of a cell sheet cutting assistance system related to the present invention comprises:

a processor for executing a program; and a storage device for storing the program, wherein the processor:

receives, as input, an evaluation standard of a cell sheet and quality information of a cultured cell sheet;

determines whether the quality information satisfies the evaluation standard; and outputs a cutting position of the cell sheet based on a result of the determination.

An example of a cell culture system related to the present invention comprises:

the above cell sheet cutting assistance system;

a culture container; and an observation apparatus for performing observation of cells or a monitoring apparatus performing monitoring of cell culture supernatant.

A cell sheet cutting assistance method related to the present invention is executed by a cell sheet cutting assistance system having a processor executing a program and a storage device storing the program, the method comprising:

receiving, as input, an evaluation standard of a cell sheet and quality information of a cultured cell sheet;

determining whether the quality information satisfies the evaluation standard; and outputting a cutting position of the cell sheet based on a result of the determination.

According to a cell sheet cutting assistance system, a cell culture system and a cell sheet cutting assistance method related to the present invention, the step for finding the portion to be cut in the cell sheet is facilitated.

BRIEF DESCRIPTION OF THE DRAWINGS

FIGS. 3A-3D show examples of tables stored in a storage device;

FIG. 4 shows an example of quality determination process for the cell sheet;

FIG. 7 shows a displayed example of a screen of the cell sheet cutting assistance system in Example 2;

FIG. 8 is a chart explaining an example of prediction result data according to the cell sheet cutting assistance system in Example 4;

DETAILED DESCRIPTION

The present invention has the following construction. Objects, feature, advantages and ideas of the present invention are clear to those skilled in the art from the descriptions of the present specification and those skilled in the art can easily reproduce the present invention from descriptions of the present specification. Embodiments, specific examples, etc. of the present invention described below indicate preferable aspects of implementation of the present invention and shown for illustration or explanation but not for limiting the present invention thereto. It is clear to those skilled in the art that various changes and modifications can be made based on the descriptions of the present specification within the intent and the scope of the present invention disclosed herein.

Embodiments of the present invention will be described below based on the accompanying drawings.

Example 1

Figures 1, 2:
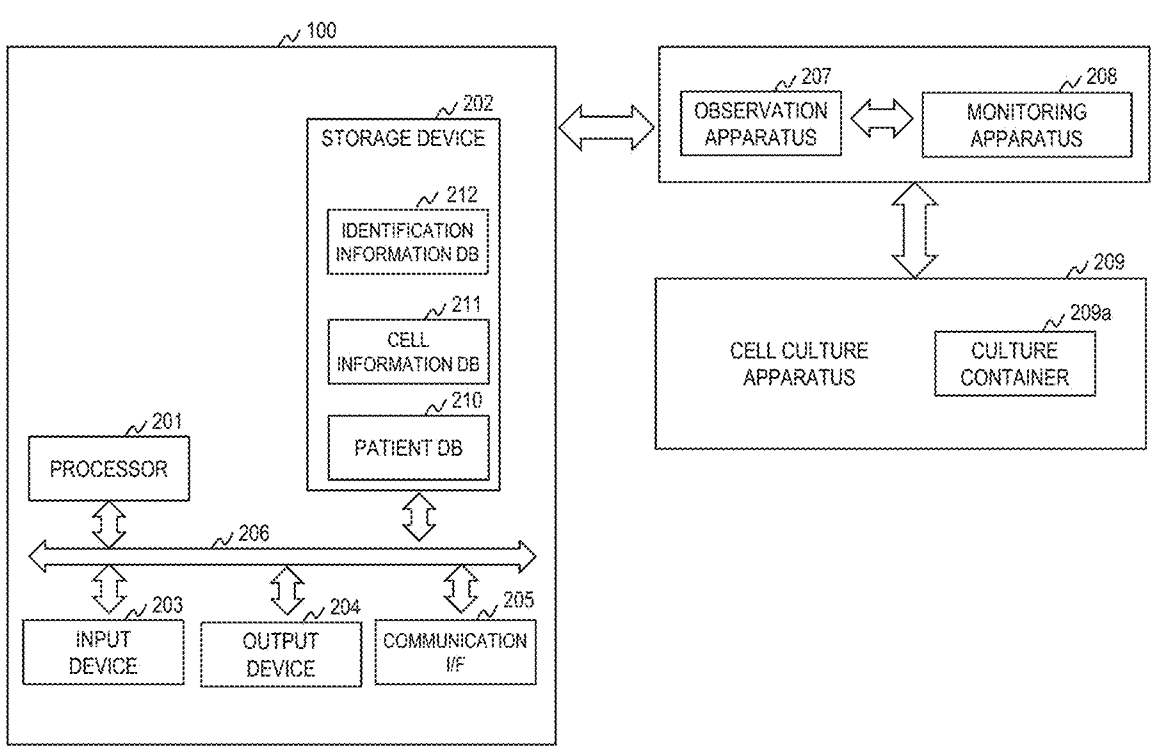
FIG. 1 shows an overview of Example 1.
FIG. 2 shows a construction example of a cell sheet cutting assistance system.

FIG. 1 is a drawing explaining an overview of a cell sheet cutting assistance system, a cell culture system and a cell sheet cutting assistance method related to Example 1 of the present invention.

For example, cell sheet cutting assistance system 100 obtains quality information and an evaluation standard of a cultured cell sheet from organization 101 (a medical institution, a pharmaceutical company, a cell sheet production company, etc.) having cell culture apparatus. Then, it outputs a cutting position of the cultured cell sheet based on the quality information and the evaluation standard as explained later.

Also, the cell sheet cutting assistance system 100 has quality information of a cell sheet corresponding to distinctive cutting positions. If it receives an inquiry of quality information of the cell sheet from the organization 101 having the cell culture apparatus, it responds with obtained quality information corresponding to the cell sheet.

In another example, in a case where the cell sheet cutting assistance system 100 cultures a cell sheet, the cell sheet cutting assistance system 100 obtains an evaluation standard of the required cell sheet from an organization 102 (a medical institution, a pharmaceutical company, etc.) not having the cell culture apparatus. The evaluation standard is, for example, obtained for each patient requesting graft of the cell sheet.

The cell sheet cutting assistance system 100 can obtain quality information of a cell sheet being cultured or after culturing at any time. The cell sheet cutting assistance system 100 calculates a cutting position of the cell sheet based on the obtained evaluation standard and quality information. Cutting operation of the cell sheet is performed by manual operation, laser, an articulated robot, etc., and the cut cell sheet is delivered. Also, by the cell sheet cutting assistance system 100, based on an identification number of the cut cell sheet, management of quality information, preservation of the cell sheet and management of transportation method may be performed.

Thus, the cell sheet cutting assistance system 100 enables cutting and dividing the cell sheet based on quality information of the cultured cell sheet.

FIG. 2 is a block diagram showing a hardware configuration and a software configuration of the cell culture system related to Example 1. The cell culture system comprises the cell sheet cutting assistance system 100, at least one of an observation apparatus 207 or a monitoring apparatus 208, and a cell culture apparatus 209. The observation apparatus 207 is an apparatus for performing observation of cells and the monitoring apparatus 208 is an apparatus for performing monitoring of the cell culture supernatant. The observation apparatus 207 and the monitoring apparatus 208 are connected to the cell sheet cutting assistance system 100 and the cell culture apparatus 209.

In accordance with such a construction, the cell culture system can perform not only assistance in cutting but also culturing of the cell sheet and observation or monitoring of the cell sheet.

The cell culture apparatus 209 has a culture container 209*a* and performs culturing of cells. The cell culture apparatus 209 may be a closed system culture apparatus or may be an enclosure-type culture apparatus. Types of cells to be cultured are not limited. Also, the cells may have a single layer or laminated multilayered structure.

The observation apparatus 207 and the monitoring apparatus 208 obtains quality information of cells being cultured or after culturing.

The observation apparatus 207 comprises, for example, a microscope such as a phase contrast microscope, a differential interference microscope, a bright-field microscope, etc. These microscopes comprise imaging devices such as CCD sensors, CMOS sensors, etc. The observation apparatus 207 generates image data by observing a cell sheet in the culture container. Then, it obtains quality information of the cell sheet based on the image data of each position in the culture container. The quality information includes, for example, whether there is a hole, a thickness, a cell density, a cell survival rate, and a time-series cell occupancy (or deltas of cell occupancy) for the cell sheet. Further, it may contain a cell breeding ratio, frequency of stem cells forming a colony, etc. Those skilled in the art can design a specific process for obtaining the quality information based on the image of cell sheet as needed based on known techniques or the like.

The monitoring apparatus 208 measures a pH and/or a component based on culture supernatant included in each culture container. Specifically, it measures culture medium components such as glucose, lactose, glutamine, glutamic acid, ammonium ion, natrium ion, potassium ion, calcium ion, partial pressure of carbon dioxide, partial pressure of oxygen, pH, exosome, RNA, DNA and protein from culture supernatant and obtains these as the quality information.

The quality information obtained by at least one of the observation apparatus 207 or the monitoring apparatus 208 is transmitted to the cell sheet cutting assistance system 100 via a network. Also, the observation apparatus 207 and monitoring apparatus 208 may have, as the quality information, information regarding a region where quality of the cell sheet is uniform.

The cell sheet cutting assistance system 100 has a processor 201, a storage device 202, an input device 203, an output device 204 and a communication interface 205. The hardware elements are connected via a bus 206.

The input device 203 is a device for inputting various information and for example a keyboard, a mouse, a touch panel, a numeric keypad, a scanner, a microphone, etc. This may include an application program or a part thereof. The input device 203 obtains an evaluation standard for a required cell sheet as input.

Preferably, the evaluation standard includes information about items same or corresponding to those of the quality information (for example, whether there is a hole, a thickness, a cell density, a cell survival rate, and a time-series cell occupancy (or deltas of cell occupancy) for the cell sheet). For example, if the evaluation standard and the quality information are configured to include information representing at least one of whether there is a hole, a thickness, a cell density, a cell survival rate, or a time-series cell occupancy of the cell sheet, the cell sheet can be evaluated appropriately. However, the evaluation standard is not limited thereto. It does not have to include all items corresponding to the quality information and it may include information about another item. In particular, the evaluation standard may include information representing a type of cell, a culture condition of cell, etc. The information representing the culture condition includes a culture period, a frequency of culture medium replacement, a monitor or observation frequency, etc.

The evaluation standard defines an allowable value or an allowable range for each item. For example, it is specified that there should be no hole, that the thickness should be equal to or more than a specific threshold thickness, that the cell density should be equal to or more than a predetermined threshold cell density, etc.

The storage device 202 is, for example, a transitory or non-transitory storage medium. The storage device 202 is constituted by, for example, a mass and non-volatile storage device such as ROM (Read Only Memory), RAM (Random Access Memory), HDD (Hard Disk Drive), a semiconductor storage device constituted by flash memory (SSD), etc. The storage device 202 stores a program executed by the processor 201, a patient database 210, a cell information database 211 and an identification information database 212.

The patient database 210 stores, as shown in FIG. 3A, data including the evaluation standard and the culture condition inputted via the input device 203. The culture condition may be included in the evaluation standard.

The cell information database 211 stores, as shown in FIG. 3B, culture container numbers ("No.") associated with position information (e.g. coordinates) of cell sheets being cultured or after culturing and quality information ("observation result" and "monitoring result") obtained from the observation apparatus 207 and the monitoring apparatus 208.

In the example of FIG. 3, items do not match completely between the evaluation standard in the patient database 210 in FIG. 3A and the quality information of the cell information database 211 in FIG. 3B. However, these may contain at least one common item. Those skilled in the art may determine specific items of the evaluation standard and the quality information as needed as explained above.

The identification information database 212 stores, as shown in FIG. 3C, regarding cut cell sheets (i.e. separate cell sheets cut and divided to be supplied to specific patients), identification numbers thereof ("No.") associated with identification information of the cut cell sheets ("identification information") and other information regarding the cell sheets.

FIG. 3D will be explained later in relation to Example 2.

The processor 201 calculates a cutting position of a cultured cell sheet based on the quality information and the evaluation standard for each cell sheet by executing a program stored in the storage device 202. For example, the processor 201 determines whether the quality information of each cell sheet satisfies any evaluation standard based on the evaluation standards included in the patient database and extracts the cell sheet (or a specific region within the cell sheet) which satisfies any evaluation standard. Then, the processor 201 calculates the cutting position for cutting the cell sheet in the extracted cell sheet or region.

An example of a determination process for the cell sheet by the processor 201 will be explained by using FIG. 4. For example, regarding a cell sheet 301, if the quality information obtained by the observation apparatus 207 satisfies the required evaluation standard (for example, cells distribute on the entire surface of the culture surface of the culture container, there is no hole in the cell sheet and the thickness is greater than the evaluation standard), the processor 201 may determine that the quality information satisfies the evaluation standard for the entire surface. In this case, the entire surface will be a range suitable for graft 304.

On the other hand, if there is no cell on a portion of the culture surface, i.e. if there is a hole 305 in the cell sheet as in a cell sheet 302, or if the thickness does not satisfy the evaluation standard in a portion because there is a thin region 306 in the cell sheet as in a cell sheet 303, the processor 201 may determine that the quality information does not satisfy the evaluation standard for those ranges. In this case, the thin region 306 is not used for graft.

Figure 4:
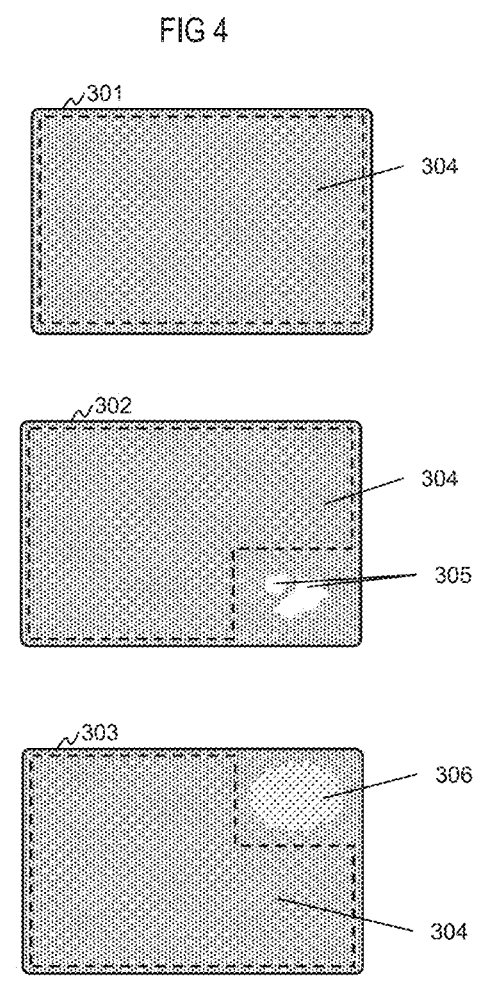

Although the determination process is performed for each region in the cell sheet in the example of FIG. 4, unit for the determination process can be designed arbitrarily. For example, the determination process may be performed for each region of a predetermined size within the cell sheet, the determination process may be performed for each cell sheet, or the determination process may be performed for each culture container. In particular, the processor 201 may determine whether the quality information satisfies the evaluation standard for each culture container based on the quality information obtained by the monitoring apparatus 208.

The communication interface 205 is connected to a network, and transmits and receives data. For example, the communication interface 205 transmits and receives various information to/from the organization 101 having the cell culture apparatus and the organization 102 not having the cell culture apparatus via the network.

The output device 204 is a device for outputting various information and for example a display, a printer, a speaker, etc. The output device 204 can output quality information of the cell sheet, a cutting position of the cell sheet, a cutting method, a cell image, etc. The information may be outputted via an application program and, for example, outputted at termination of culturing the cell sheet or at any timing requested by a user.

Figure 5:
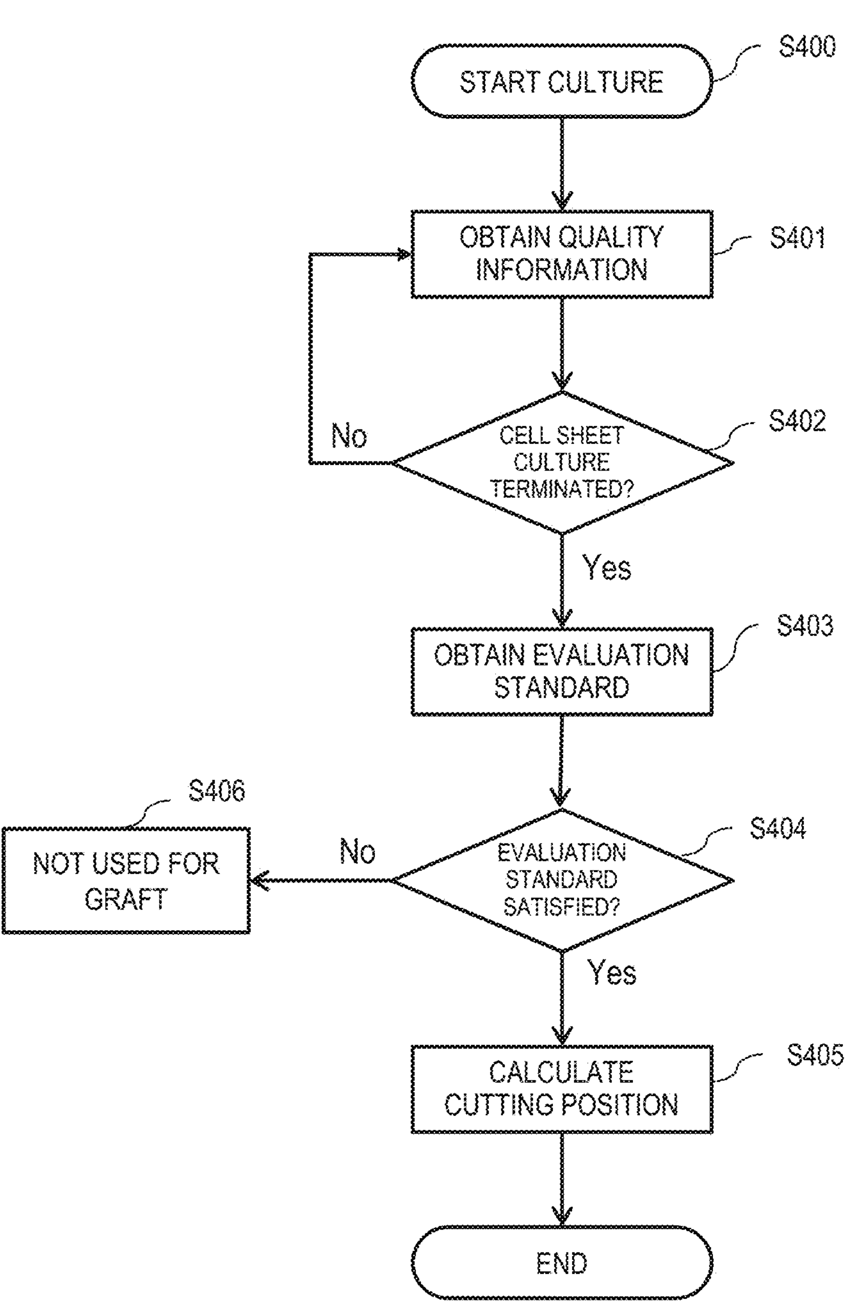
FIG. 5 is a flowchart in Example 1.

FIG. 5 is a flowchart explaining a process flow in the cell sheet cutting assistance system 100. FIG. 6 shows diagrams of examples of screens outputted by the cell sheet cutting assistance system 100.

First, culturing of a cell sheet is started by the cell culture apparatus (S400). During culture, the cell sheet cutting assistance system 100 obtains the quality information of the cell sheet obtained by the observation apparatus 207 and the monitoring apparatus 208 (S401).

Figure 6A:
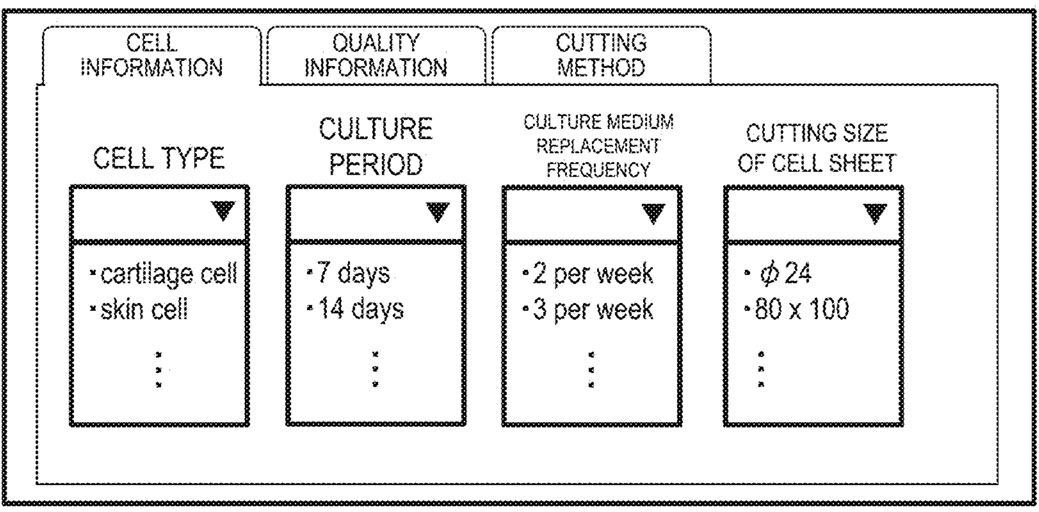
FIGS. 6A-6C show displayed examples of screens of the cell sheet cutting assistance system in Example 1.
Figure 6B:
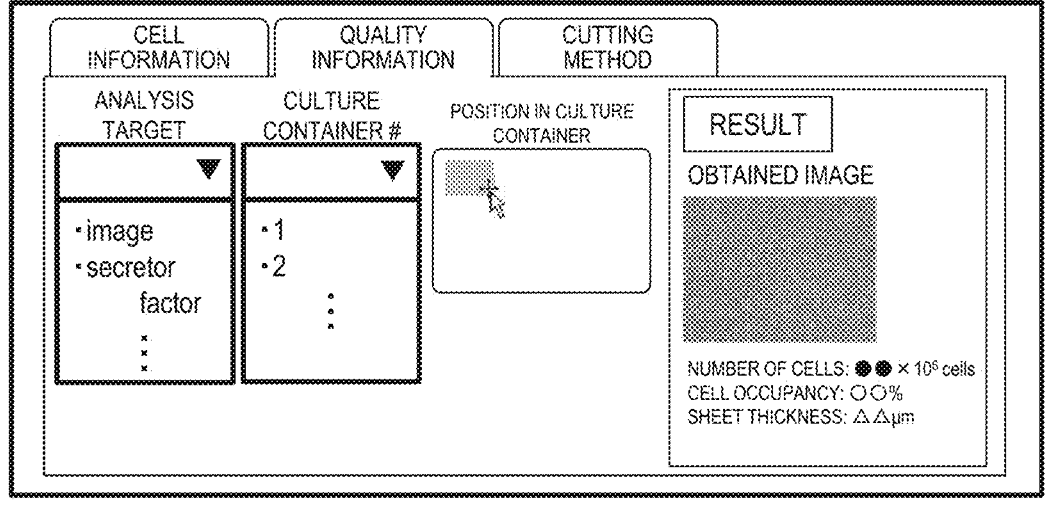

In S401, the cell sheet cutting assistance system 100 may output cell information and/or quality information being cultured or after culturing on a screen as shown in FIGS. 6A and 6B. FIG. 6A shows a list of the quality information and FIG. 6B shows an image of a cell sheet. The cell sheet cutting assistance system 100 may receive input of an analysis target and a culture container number as a retrieval condition as shown FIG. 6B and display an image of the corresponding cell sheet and a position in the culture container as a retrieval result. According to such a screen display, the user can confirm the cell sheet to be grafted to the patient by referring to the screen.

It is determined as to whether the culturing of the cell sheet is terminated (S402), and if the culturing of the cell sheet is not terminated, S401 and S402 are repeated. If it is determined that the culturing of the cell sheet is terminated, the processor 201 receives an evaluation standard of a cell sheet for each patient from the patient database 210 as input (S403, an inputting process). As to the evaluation standard, one stored in the storage device 202 in advance may be inputted or a new one may be inputted via the input device 203.

Then, the processor 201 determines whether the quality information satisfies the evaluation standard for each cell sheet (S404, a determination process). Unit of determination can be determined arbitrarily as explained above. For example, it is determined, regarding all the patients, the quality information of a cell sheet satisfies the evaluation standard for respective patients. A cell sheet (or a specific region therein) whose quality information does not satisfy any evaluation standard can be considered to be not suitable for graft and is not used for graft (S406). The latest quality information may be obtained again between S403 and S404.

The processor 201 outputs (S405, an outputting process) a cutting position of the cell sheet based on a result of S404 (the determination process). For example, it extracts one cell sheet or a specific region therein from among the cell sheets whose quality information satisfies the evaluation standard of any patient and calculates the cutting position based on the extracted cell sheet or region. Those skilled in the art can design a standard for extracting one cell sheet or region in a case where the quality information of a plurality of cell sheets or regions satisfy the evaluation standard of a particular patient.

Figure 6C:
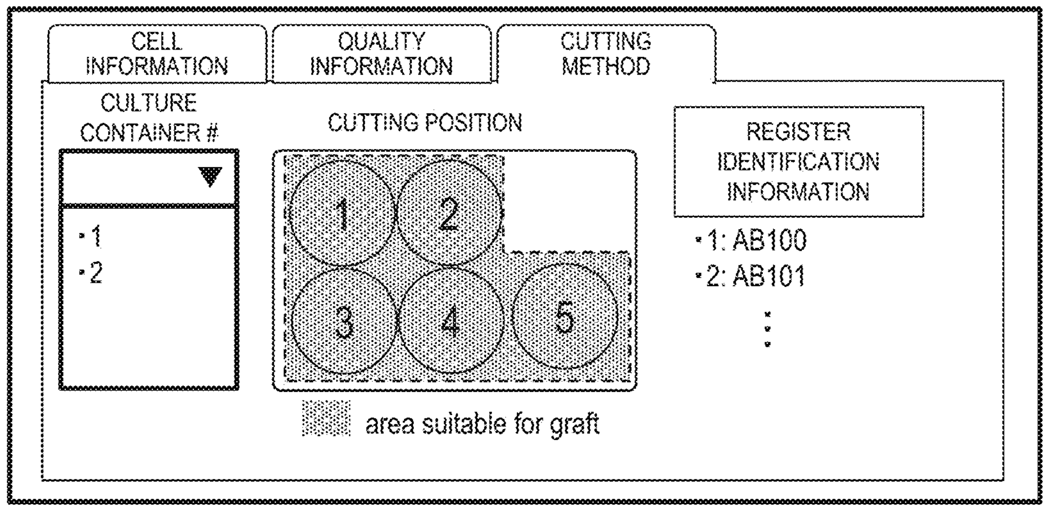

The output device 204 may output the cutting position as shown in FIG. 6C. FIG. 6C shows an example of a case wherein five circular regions are cut for graft from a cell sheet. For a certain cell sheet, the region wherein the quality information satisfies the evaluation standard is indicated in gray, and in that region, regions to be cut are indicated with numbers 1-5 assigned.

A method for determining a region (surface) to be cut or a position (line) to be cut in the cell sheet or region can be designed by those skilled in the art as needed. As an example of a simple method, in the example of FIG. 6C, it can be determined as follows: a predetermined cutting shape is arrayed in one row from top left to right in the cell sheet or region, and if a next cutting shape is not to be contained within the cell sheet or region at the right edge thereof, the predetermined cutting shape is arrayed in one row immediately below the previous row from left to right, and so on.

After the cutting position is outputted to the output device 204, the cell sheet is cut. The cutting of the cell sheet is not limited in any way. A human operator may perform this manually or by using a tool, or the cell sheet cutting assistance system 100 or the cell culture apparatus 209 may perform this automatically.

Specific examples may be methods using a cutting jig wherein a scalpel, scissors, die cutting, laser, plasma wave, ultrasonic wave, etc., is used. In a case of cutting by a scalpel, scissors or a jig, an operator cuts the cell sheet at a safety cabinet based on the cutting position calculated by the processor 201.

In a case wherein the cell culture apparatus 209 has a cutting apparatus of the cell sheet by laser, plasma wave, ultrasonic wave, etc., the cell culture apparatus 209 may be constructed such that the cell culture apparatus 209 makes the cutting apparatus read information of the cutting position according to the cutting position calculated by the processor 201 so that the cutting apparatus irradiates the laser or the like in order to cut the cell sheet. The cut cell sheet is processed to be dissected from the container by any method, enclosed in an individual packaging container, and transported.

These steps may be performed automatically using an articulated robot installed in a safety cabinet. Note that, a cell sheet in the present example may include a cell organization or a three-dimensional organization.

The cell sheet cutting assistance system 100 constructed as above extracts a region of a cell sheet suitable for graft based on the evaluation standard of a cell sheet and the quality information of the cultured cell sheet and calculates the cutting position of the cell sheet from the extracted region. Thus, the operator can easily grasp the cutting position of the cell sheet, so the step for finding the portion to be cut in the cell sheet is facilitated.

As a modified example of Example 1, the cell sheet cutting assistance system 100 may receive, as input, a number and/or a shape of the cell sheet to be cut associated with the evaluation standard at S403 (the inputting process). Then, it is also possible to calculate the cutting position based on the number and/or shape in the cell sheet or region wherein the quality information satisfies the evaluation standard as shown in FIG. 6C. In this case, the extracted region can be used more efficiently.

Example 2

In Example 2, the cutting position of the cell sheet is calculated further based on patient information in addition to Example 1. Example 2 will be explained below focusing on differences from Example 1.

In Example 2, the input device 203 further receives, as input, patient information of a patient to whom the cell sheet is grafted at S403 (the inputting process). The evaluation standard may be associated with the patient information.

As a specific example, the patient information includes information representing a number, a size and a shape of the cell sheet to be grafted (this information may constitute a part of the evaluation standard). Further, this may include information such as a patient ID (identifier), a name of the medical institute related to graft, a size of an affected part, a name of disease, reservation information, cancellation information of a graft operation, etc. The shape of the cell sheet can be defined in response to a form, a size and a condition of the affected part of the patient, and is, for example, a circle, an ellipse, a tetragon, a polygon, etc.

As shown in FIG. 3D, the patient database 210 is inputted via the input device 203 and stores data including the patient information including a patient ID, the evaluation standard and the culture condition for each patient associated for each patient. The evaluation standard and the culture condition may include items same as Example 1 (FIG. 3A).

A flow of the process of the cell sheet cutting assistance system of Example 2 is the same as Example 1 except for a partial difference in the calculation method of the cutting position.

At S403, the processor 201 of the cell sheet cutting assistance system 100 obtains the patient information regarding a plurality of patients scheduled for cell sheet graft from the patient database 210. Then, at S405, the processor 201 calculates the cutting position of the cell sheet after culturing based on the obtained patient information for the region that satisfied the evaluation standard at S404.

The patient database 210 used at S405 can be obtained at any time from before culturing of the cell sheet to termination of culturing thereof.

If a graft operation for a patient scheduled for the graft is canceled, the processor 201 may receive cancellation information of the cell sheet as input at S403. The cancellation information is, for example, information representing that a graft of the cell sheet for a first patient has been canceled.

If the graft of the cell sheet for any patient is canceled, the processor 201 may receive, as input, a patient who receives an operation instead, i.e. a second patient to whom the cell sheet is grafted, from the patients recorded in the patient database 210. The second patient may be specified by identification information being inputted from the input device 203 or automatically selected and specified by the processor 201.

If the processor 201 obtained the patient information of the second patient, it receives the evaluation standard associated with the patient information of the second patient as input.

Then, the processor 201 determines whether the quality information of the cultured cell sheet satisfies the evaluation standard of the selected patient (for example the first patient, but may be the second patient if the cancellation occurs), and if it does, outputs the cutting position of the cell sheet based on the patient information of the selected patient.

The cutting position is outputted via the output device as shown in FIG. 7. Note that those skilled in the art can design a method for determining the specific cutting position based on the shape and size based on known techniques or the like.

In Example 2, it is determined as to whether the quality information of the cultured cell sheet satisfied the evaluation standard of the selected specific patient individually, and if it does not, a new patient is again selected from the patient database 210 and a similar determination process is repeated. The selected new patient may be a patient newly inputted via the input device. Note that those skilled in the art can design specific steps for comparing the quality information and the evaluation standard, and for example, the determination processes for all patients may be performed at once in a manner similar to Example 1.

The cut cell sheet is moved from the container to an individual packaging container, enclosed therein and transported in any method. The enclosing and transporting may be performed based on patient information such as medical institute information related to the graft.

The cell sheet cutting assistance system constructed as above outputs the cutting position for use in graft for a plurality of patients from the quality information of the cultured cell sheet based on the evaluation standard of the cell sheet and the patient information, so each patient can be assigned an optimal cell sheet. In particular, cell sheets having various shapes and sizes can be cut efficiently in response to requested shapes, sizes and numbers. Thus, loss of cell sheets can be reduced and waste amount of unused cell sheets can be reduced.

Also, in a construction that receives the cancellation information, if a patient cancels graft of a cell sheet, the cell sheet can be grafted to another patient, so the loss of cell sheets can be further reduced and the waste amount of unused cell sheets can be further reduced.

Example 3

In Example 3, identification information is assigned to the cut cell sheet based on the calculated cutting position in addition to Example 1 or 2. Example 3 will be explained below focusing on differences from Example 1.

The cell sheet is cut based on the cutting position outputted by the cell sheet cutting assistance system 100, packaged in an individual packaging container and transported. Identification information (an identification number, an identifier, etc.) of the cut cell sheet is assigned to the individual packaging container.

The identification information is information generated for each of the cut cell sheets as shown in FIG. 3C, and can be associated with the quality information during culturing or after culturing and/or the patient information. The storage device 202 stores the quality information of the cut cell sheets associated with the identification information. Also, the processor 201 may be able to perform a process for receiving the identification information as input and a process for outputting the quality information of the cell sheet associated with the identification information. In this way, the quality information of a cut cell sheet can be outputted in response to the operator reading and inputting the identification information displayed at the cut cell sheet.

Any specific display method can be adopted for the identification information for the cell sheet, and for example the identification information may be displayed directly on the cell sheet or may be assigned to a supporting body used for handling in dissecting, transporting, etc. of the cell sheet. Any one or more of identification code (text information, a one-dimensional barcode, a two-dimensional barcode, a QR code (registered trademark), an RFID tag, etc.) can be selected and assigned to the supporting body. For example, if the text information and the RFID tag are assigned, the operator can recognize the text information and an electronic reader or the like can recognize the RFID tag. As a method for assigning the identification code, a method of engraving predetermined shapes directly on an individual packaging container of the supporting body, a method of printing letters by ink by using a laser printer, a method of embedding a tag or a chip, etc. can be selected. It is preferable that the selected method does not exhibit any cytotoxicity and is capable of sterilization.

Thus, in Example 3, the identification information associated with the quality information is assigned to each of the cut cell sheets, so the quality information of the cell sheet can be traced even after the cell sheet is grafted to the patient. Accordingly, the quality information can be referred to based on the identification information as needed, for example.

Example 41

In Example 4, at the calculation of the cutting position of the cell sheet (S405), the cutting position of the cell sheet is calculated considering not only the quality information of the cell sheet and the patient information described in Example 2 but also prognosis information of patients after grafting cell sheets. Example 4 will be explained below focusing on differences from Example 2.

A hardware construction of the cell sheet cutting assistance system of Example 4 can be the same as that of Example 1 or 2.

The input device 203 receives prognosis information of the patient to whom the cell sheet has been grafted as input. The prognosis information obtained by the input device 203 is stored in a prognosis information database of the storage device 202.

FIG. 8 shows an example of the prognosis information database storing the prognosis information. The prognosis information includes, as a specific example, a patient ID, a cell type of the grafted cell sheet, a size of the affected part, a size of the grafted cell sheet, a treatment effect for the patient by the graft, etc. Also, the prognosis information may include an identification number of the grafted cell sheet, a number of cell sheets used for graft, an anamnesis of the patient, a treatment implemented after grafting the cell sheet, etc. The evaluation standard and the culture condition may contain items same as Example 1 (FIG. 3A).

Figure 9:
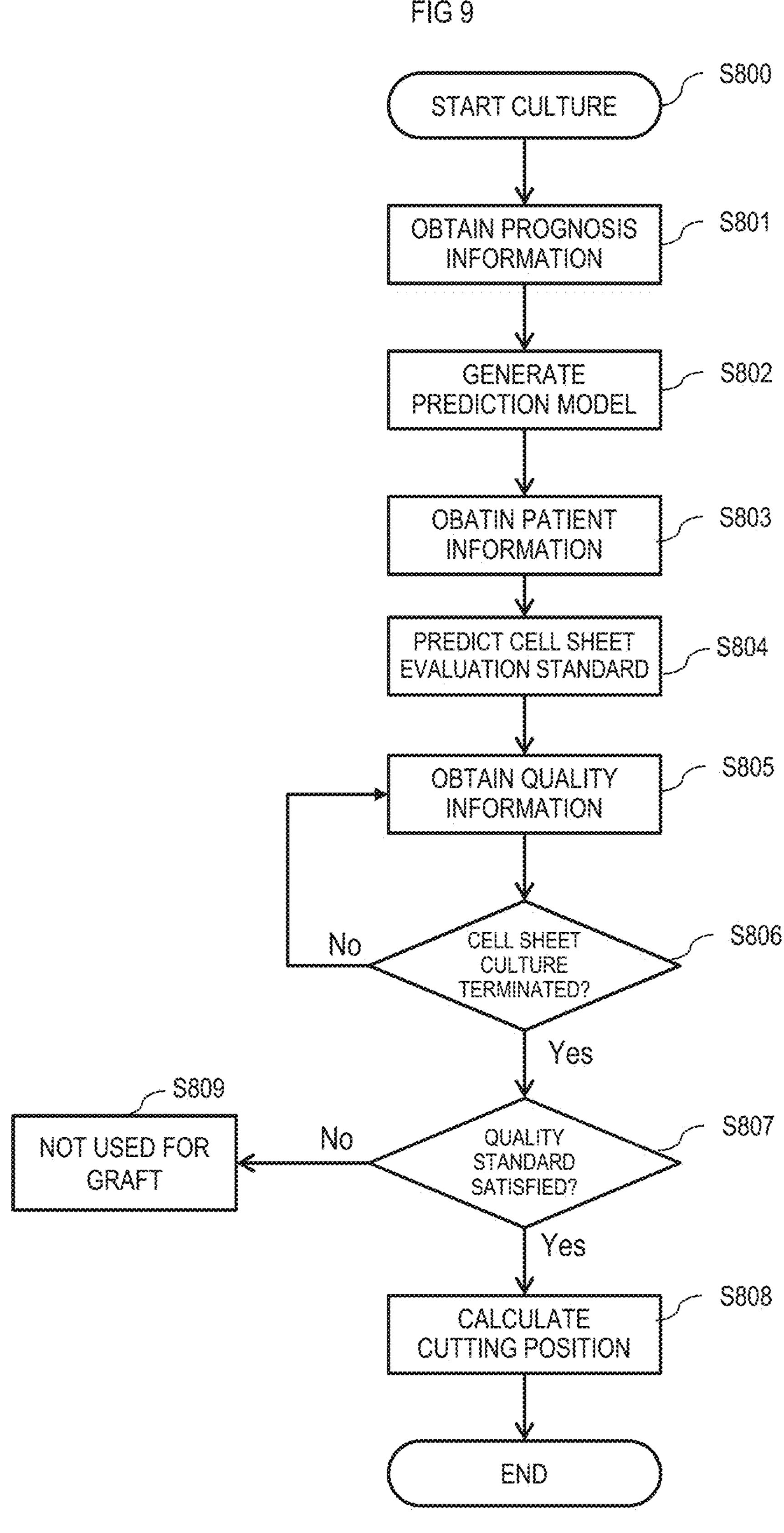
FIG. 9 is a flowchart showing an output example of a cutting position in Example 4.

A flow of process of the cell sheet cutting assistance system of Example 4 is shown in FIG. 9.

First, culturing of a cell sheet is started by the cell culture apparatus (S800). The processor 201 receives, as input, the prognosis information of the patient to whom a cell sheet is grafted and the quality information of the grafted cell sheet via the input device 203 (S801).

Next, the processor 201 generates a prognosis information prediction model by machine learning (S802). The prognosis information prediction model is, for example, a model for predicting a treatment effect based on the prognosis information (excepting the treatment effect). A well-known or known approach such as neural network or logistic regression can be adopted for the model of machine learning, which is not detailed here.

Although configuration of the prognosis information can be designed by those skilled in the art as needed, it may be as shown in FIG. 8, it may include items same as the entire quality information or a part thereof, it may include items same as the entire evaluation standard or a part thereof, or it may include items same as the entire patient information or a part thereof. The treatment effect is a value that can be determined by personnel or the like of the medical institute related to the graft and for example represents a probability (percentage) that a disease is cured.

Next, the processor 201 receives the patient information as input (S803).

Next, the processor 201 may calculate the evaluation standard of the cell sheet suitable for the patient by inputting the obtained patient information to the prognosis information prediction model (S804). Note that, as explained below, S804 can be omitted in a case where a process for selecting the cell sheet for which the treatment effect is estimated to be maximum is performed in S808.

The processor 201 obtains the quality information of the cell sheet (S805), determines whether culturing of the cell sheet is terminated (S806), and determines whether the quality information satisfies the evaluation standard (S807) in a manner similar to Example 1. The evaluation standard of each patient may be obtained at or before S807. Cell sheets (or specific regions thereof) whose quality information does not satisfy the evaluation standard are not used for grafting (S809).

Then, the processor 201 outputs the cutting position of the cell sheet (S808) based on a result of S807. Here, if one cell sheet satisfies evaluation standards of a plurality of patients, the processor 201 selects an optimal patient by using the prognosis information prediction model. For example, the processor 201 estimates a treatment effect for each patient by inputting the patient information of the patient (for example, the prognosis information shown in FIG. 8 excepting the patient ID and the treatment effect) to the prognosis information prediction model and determines the patient for whom the treatment effect is highest as the graft target.

If the evaluation standard of the patient is not fixed or the evaluation standard is determined to be inappropriate (e.g. the cell sheet is too large or too small, etc.), the cell sheet cutting assistance system 100 may output recommendation related to the size of cell sheet suitable for the patient, the evaluation standard, etc. based on the prognosis information prediction model.

Thus, in Example 4, paring between the cell sheet and the patient can be more optimized by using the prognosis information of patients after graft.

Example 51

In Example 5, the cell sheet cutting assistance system 100 has a light source and outputs the cutting position by using the light source in addition to Example 1. Example 5 will be explained below focusing on differences from Example 1.

Figure 10:
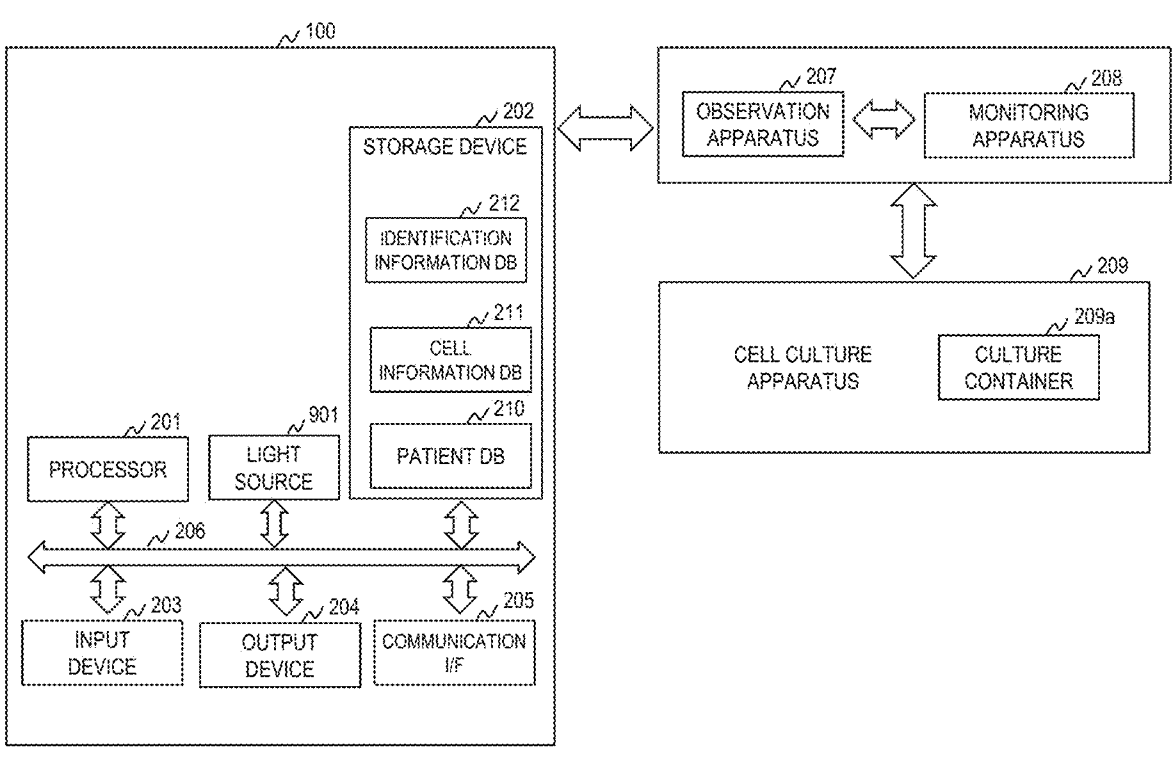
FIG. 10 shows a construction example of a cell sheet cutting assistance system in Example 5.

FIG. 10 shows a block diagram of the cell sheet cutting assistance system 100 in Example 5. The cell sheet cutting assistance system 100 of Example 5 comprises a light source 901 in addition to the construction of Example 1 (FIG. 2). The light source 901 projects light to the cutting position of the cultured cell sheet based on the cutting position of the cell sheet calculated by the processor 201. The light source 901 may correspond to the output device 204 (FIG. 2).

Figure 11A:
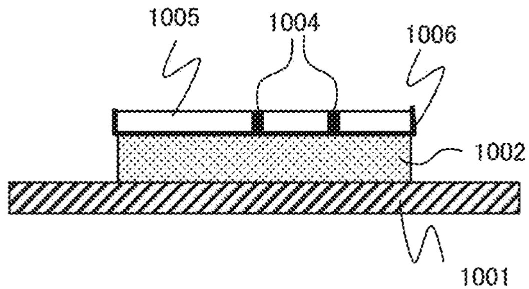
FIGS. 11A-11C show diagrams explaining installation examples of light sources of the cell sheet cutting assistance system in Example 5.

FIG. 11 shows examples of installation of the light source. In the example of FIG. 11A, a light projector 1002 including the light source is installed under a transparent culture container 1006. The light projector 1002 is for example a liquid crystal display device and projects light upwardly. The light projector 1002 includes may light sources (e.g. light emitting elements), so it can be said that light sources are installed at plurality of locations below the cell sheet 1005. The light projector 1002 projects light on the cutting positions 1004 of the cell sheet 1005 as shown in FIG. 12. The operator can cut the cell sheet 1005 along the cutting positions 1004, so the step for finding the portion to be cut in the cell sheet is facilitated.

Lights from the light source 901 may be in different colors for respective cell sheets or respective cell types in the cell sheet cutting step. Also, projected content may be indicated by different signs or symbols for respective identification information of the cell sheet or respective cell types. Further, operation content for the operator may be indicated. Thus, the operator can obtain more information by constructing the light source 901 so that it projects one or more types of color, sign, symbol or operation content.

Also, in a cell sheet packaging step, the light source 901 may project identification information of the individual packaging container on the cut cell sheet to be packaged therein. The light source 901 may project a cell sheet which needs an operation such as cutting or transportation in response to time. In addition, the cell sheet cutting assistance system 100 may have a sensor and may be constructed to detect an error by the sensor and issue an alert by the light if the operator attempts to cut a position different from the cutting position 1004.

Thus, in Example 5, information can be assigned on the cell sheet in a non-invasive manner by outputting the cutting position of the cell sheet by light, so the step for finding the portion to be cut in the cell sheet is facilitated, and therefore, reduction of erroneous operation of the operator and improvement of operation efficiency can be realized.

Also, in Example 5, information can be assigned to the cell sheet in a non-invasive manner, so if a graft operation is canceled and a portion of the patient to whom the cell sheet is grafted is changed immediately before the operation, displayed content of the cutting position can be changed easily and promptly.

Figure 11B:
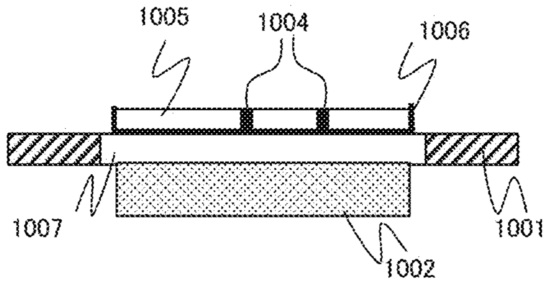
Figure 11C:
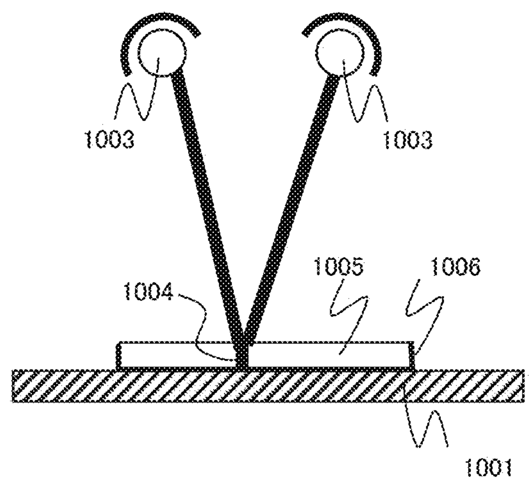
Figure 12:
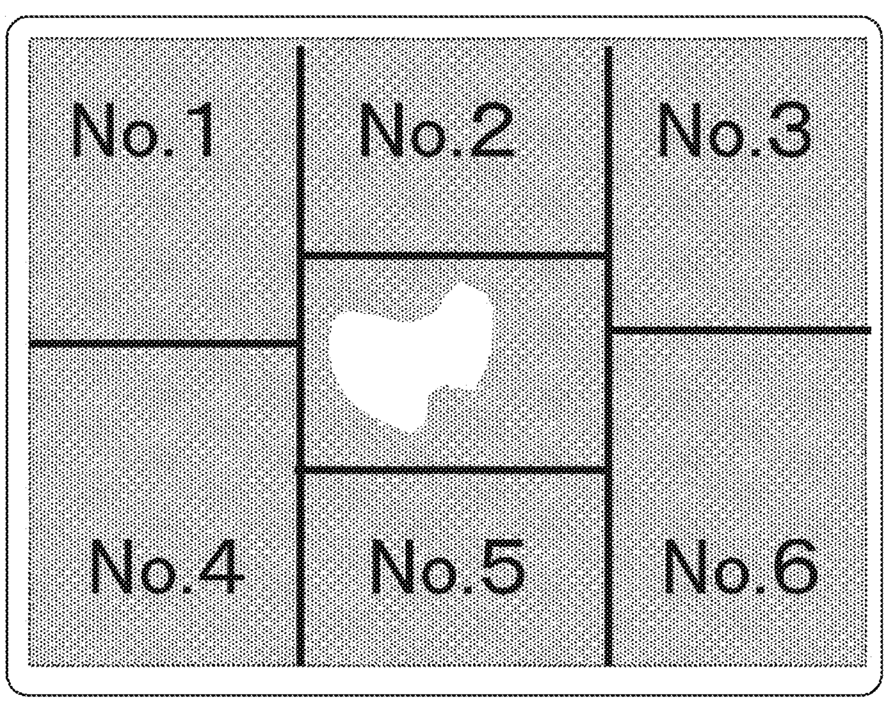
FIG. 12 is a diagram showing an example of light projection by the light source in Example 5.

In addition, as specific installation manners of the light source 901, constructions shown in FIG. 11B or 11C can be considered.

FIG. 11B shows an exemplary construction wherein the light projector 1002 including the light source is installed on a bottom portion of the floor plate of the safety cabinet 1001 and light from the light projector 1002 is irradiated to the cell sheet 1005 via a light transmitting window 1007. In this construction, a bottom surface of the culture container 1006, which is an operation position, is located at a height approximately the same as a top surface of the safety cabinet 1001, so operation efficiency is improved.

FIG. 11C shows an exemplary construction wherein the plurality of light sources 1003 installed above an operation space project light on the cell sheet 1005 from a plurality of directions. In this construction, even if light from one light source 1003 is blocked by hitting a hand of the operator or the like upon an operation, light from another light source 1003 is projected on the cell sheet 1005, so it is possible to assign information such as the cutting position as explained above more securely.

Note that, because the hand of the operator is located above the cell sheet 1005, such an effect can be substantially obtained even in a case where the light projector 1002 is installed below the cell sheet 1005 as shown in FIG. 11A or 11B. Same can be said for a case wherein a single light source 1003 is installed below the cell sheet 1005. Thus, it is preferable to install the light sources at one or more locations below the cell sheet 1005 or to install the light sources at two or more locations above the cell sheet 1005.

The cell sheet cutting assistance system 100 may cut the cell sheet 1005 automatically by the light from the light sources 1003 shown in FIG. 11C. For example, laser may be used as the light from the light sources 1003 and the laser may output the cutting position 1004 and, at the same time, cut the position. In this way, the step for finding the portion to be cut in the cell sheet is further facilitated. Also, the cutting operation is automated and operation efficiency is improved.

Thus, according to the cell sheet cutting assistance systems related to above Examples 1-5, the step for finding the portion to be cut in the cell sheet is facilitated. Also, because of this, cutting efficiency of the cell sheet is improved. Further, according to Example 4, treatment effect is improved.

Note that the present invention is not limited to the above Examples but includes various modifications and equivalent constructions within gist of appended claims. For example, above Examples are explained in detail for facilitating understanding the present invention and the present invention is not limited to those comprising all the explained constructions. Also, a part of the construction of an Example may be substituted by a construction of another Example. Also, a construction of an Example may be added to a construction of another Example. Also, a part of constructions of the Examples may be subject to addition, deletion or replacement with another construction.

Also, the above constructions, functions, processing portions, processing means, etc. may be realized in hardware by e.g. designing a part or all of them with, for example, integrated circuits or in software by a processor interpreting and executing a program realizing respective functions.

Information such as programs, tables, files, etc. realizing the functions may be stored on a storage device such as a memory, a hard disk, an SSD (Solid State Drive), etc., or a storage medium such as an IC (Integrated Circuit) card, an SD card and a DVD (Digital Versatile Disc).

A client such as a hospital, a pharmaceutical company and a cell sheet producing company may perform a series of operations including accepting an order of a cell sheet, culturing of the cell sheet, packaging and transportation by using the cell sheet cutting system related to the Examples of the present invention. As a specific embodiment, if a cell sheet cutting assistance system receives an order of a cell sheet and a scheduled delivery date from the hospital, the pharmaceutical company or the cell sheet producing company, it configures a condition required for culture in accordance with the scheduled delivery date and operates a cell culture apparatus based on the condition. Quality information of the cell sheet is obtained during culture as described above. After termination of cell sheet culture, an operator assigned by the cell sheet cutting assistance system cuts, dissects, packages and transports the cell sheet based on the cutting position of the cell sheet outputted on a screen. The hospital, the pharmaceutical company or the cell sheet producing company can receive the cell sheet cultured based on ordered content.

DESCRIPTION OF SYMBOLS

100 cell sheet cutting assistance system
101 organization having cell culture apparatus
102 organization not having cell culture apparatus
201 processor
202 storage device
203 input device
204 output device
205 communication interface
206 bus
207 observation apparatus
208 monitoring apparatus
209 cell culture apparatus
209*a* culture container
210 patient database
211 cell information database
212 identification information database
301-303 cell sheets
304 range suitable for graft
305 hole
306 thin region
901 light source
1001 safety cabinet
1002 light projector
1003 light source
1004 cutting position
1005 cell sheet
1006 culture container
1007 light transmitting window

What is claimed is:

1. A cell sheet cutting assistance system comprising:
a processor for executing a program; and
a storage device for storing the program,
wherein the processor:
receives, as input, an evaluation standard of a cell sheet and quality information of a cultured cell sheet;
determines whether the quality information satisfies the evaluation standard; and
outputs a cutting position of the cell sheet based on a result of the determination,
wherein the evaluation standard and the quality information include information representing at least one of:
whether there is a hole;
a thickness;
a cell density;
a cell survival rate; or
a time-series cell occupancy,
regarding the cell sheet,
wherein the processor further receives patient information of a patient to whom the cell sheet is grafted as input, and
wherein the evaluation standard is associated with the patient information.

2. A cell sheet cutting assistance system comprising:
a processor for executing a program; and
a storage device for storing the program,
wherein the processor:
receives, as input, an evaluation standard of a cell sheet and quality information of a cultured cell sheet;

determines whether the quality information satisfies the evaluation standard; and outputs a cutting position of the cell sheet based on a result of the determination, wherein the processor receives a number of the cell sheets as input.

3. The cell sheet cutting assistance system according to claim 1, wherein the patient information includes information representing a number, a size and a shape of the cell sheet to be grafted.

4. The cell sheet cutting assistance system according to claim 1, wherein the processor further receives, as input:

cancellation information of the cell sheet representing that graft of the cell sheet for a first patient has been canceled;

patient information of a second patient to whom the cell sheet is grafted, and an evaluation standard associated with patient information of the second patient.

5. The cell sheet cutting assistance system according to claim 1, wherein the processor further:

receives prognosis information of a patient to whom the cell sheet has been grafted and quality information of the grafted cell sheet as input and generates a prognosis information prediction model by machine learning;

receives the patient information as input; and inputting the patient information to the prognosis information prediction model.

6. The cell sheet cutting assistance system according to claim 1, wherein the storage device stores quality information of a cut cell sheet associated with identification information, and wherein the processor:

receives the identification information as input; and outputs the quality information of the cell sheet associated with the identification information.

7. The cell sheet cutting assistance system according to claim 1, wherein the cell sheet cutting assistance system comprises a light source and the light source projects light on the cutting position.

8. The cell sheet cutting assistance system according to claim 7, wherein the light source is installed at:

one or more locations below the cell sheet; or two or more locations above the cell sheet.

9. The cell sheet cutting assistance system according to claim 7, wherein the light source projects one or more types of color, sign, symbol or operation content.

10. The cell sheet cutting assistance system according to claim 7, wherein the cell sheet cutting assistance system cuts the cell sheet by the light.

11. A cell culture system comprising:

the cell sheet cutting assistance system according to claim 1;

a culture container; and an observation apparatus for performing observation of cells or a monitoring apparatus performing monitoring of cell culture supernatant.

12. A cell sheet cutting assistance method executed by a cell sheet cutting assistance system having a processor executing a program and a storage device storing the program, the method comprising:

receiving, as input, an evaluation standard of a cell sheet and quality information of a cultured cell sheet;

determining whether the quality information satisfies the evaluation standard; and outputting a cutting position of the cell sheet based on a result of the determination, wherein the evaluation standard and the quality information include information representing at least one of:

whether there is a hole;

a thickness;

a cell density;

a cell survival rate; or a time-series cell occupancy, regarding the cell sheet, and wherein the processor receives a number of the cell sheets as input.

13. The cell sheet cutting assistance method according to claim 12, wherein the processor further receives patient information of a patient to whom the cell sheet is grafted as input, and wherein the evaluation standard is associated with the patient information.

14. The cell sheet cutting assistance method according to claim 13, wherein the patient information includes information representing a number, a size and a shape of the cell sheet to be grafted.

15. The cell sheet cutting assistance method according to claim 13, wherein the processor further receives, as input:

cancellation information of the cell sheet representing that graft of the cell sheet for a first patient has been canceled;

patient information of a second patient to whom the cell sheet is grafted, and an evaluation standard associated with patient information of the second patient.

16. The cell sheet cutting assistance method according to claim 13, wherein the processor further:

receives prognosis information of a patient to whom the cell sheet has been grafted and quality information of the grafted cell sheet as input and generates a prognosis information prediction model by machine learning;

receives the patient information as input; and inputting the patient information to the prognosis information prediction model.

17. The cell sheet cutting assistance method according to claim 12, wherein the storage device stores quality information of a cut cell sheet associated with identification information, and wherein the processor:

receives the identification information as input; and outputs the quality information of the cell sheet associated with the identification information.

* * * * *